United States Patent [19]

Cooke

[11] 4,210,670
[45] Jul. 1, 1980

[54] ANTITHROMBOTIC AGENTS

[75] Inventor: Ernest Cooke, London, England

[73] Assignee: Astra Lakemedel Aktiebolag, Sodertalje, Sweden

[21] Appl. No.: 918,476

[22] Filed: Jun. 23, 1978

[30] Foreign Application Priority Data

Jul. 6, 1977 [SE] Sweden ............................... 7707867

[51] Int. Cl.² .......................................... A61K 31/165
[52] U.S. Cl. .................................................... 424/324
[58] Field of Search ........................................ 424/324

[56] References Cited
U.S. PATENT DOCUMENTS 3,337,406  8/1967  Marco et al. .......................... 424/324

OTHER PUBLICATIONS

Laaksonen et al. "Effect of Anaesthesia on the Incidence of Postoperative Lower Limb Thrombosis".
Chem. Abst., vol. 84, No. 174006f, McDevitt et al., (1976).
Chem. Abst., vol. 85, No. 56502n, Lalka et al., (1976).
Chem. Abst., vol. 71, No. 100120y, Robison et al. (1969).

Primary Examiner—Stanley J. Friedman
Attorney, Agent, or Firm—Brumbaugh, Graves, Donohue & Raymond

[57] ABSTRACT

The invention relates to a method for prophylactic treatment in order to eliminate the formation of tromboses and embolis in deep veins after surgical incisions in lower body regions, whereby a local anesthetic compound of the group consisting of lidocaine, mepivacaine, bupivacaine, tocainide, prilocaine, and ethidocaine is administered, as well as pharmaceutical preparations herefore.

7 Claims, No Drawings

ANTITHROMBOTIC AGENTS

The present invention relates to a method of prophylaxis of postoperative deep vein thrombosis in mammals including humans.

The object of the present invention is to obtain a method of prophylaxis in patients having been operated on, in order thereby to prevent the occurence of postoperative deep vein thrombosis.

It is a well known fact that the risk of deep vein thrombosis is very high after operations. Thus hip surgery, gynecological surgery and abdominal surgery induce the formation of deep vein thrombosis, which may be serious per se but is still more serious when the thrombosis starts to move towards the heart, where it lodges in the circulatory system of the lung and forms a pulmonary embolus. The thrombosis generally occurs in the veins of the lower extremities, such as in the common and external iliac, common femoral, superficial femoral, popliteal, posterior tibial and soleal veins.

In order to treat this risk of thrombosis prophylacticly medical health exercises and/or treatment with heparin, the response to which is unpredictable and carries the risk of serious haemorrhage, is carried out. Although such treatment is carried out serious postoperative deep vein thrombosis and embolism occurs in too many cases, even during therapy with this substance.

It is thus of common interest to reduce the risk of deep vein thrombosis and pulmonary embolism in order to eliminate unnecessary suffering and to reduce the numbers of days in hospital, where each day costs society and the individual much.

It has now surprisingly been found that it is possible to reduce such postoperative deep vein thrombosis to a very great extent and at least to reduce the most serious types of deep vein thrombosis by means of the present invention which is characterized in that one administers a therapeutically effective amount of a compound selected from the group consisting of 1-butyl-2(2',6'-xylylcarbamoyl)piperidine, diethylaminoacet-2',6'-xylidide, (±)-1-methyl-2-(2',6'-xylylcarbamoyl)piperidine, 2-propylamino-N-(2'-tolyl)propionamide, 2-amino-2',6'-propionoxylidide. 2-ethylpropylamino-2,6-n-butyroxylidide, or a therapeutically acceptable salt thereof.

According to a preferred embodiment of the invention the therapeutic agent is administered intravenously.

According to a further preferred embodiment of the invention, diethylaminoacet-2',6'-xylidide or 2-propylamine-N-(2'-tolyl)propionamide is administered.

According to another preferred embodiment of the invention the therapeutic agent is administered at a rate of 2 mg/minute from 2 hrs pre surgery and to 144 hrs post surgery.

According to another preferred embodiment of the invention the therapeutic agent is administered as an intravenous bolus injection of 1 mg/kg bodyweight 2 hrs pre surgery followed by a continuous intravenous injection of 2 mg/minute from 2 hrs pre surgery to 144 hrs post surgery.

According to a further preferred embodiment the bolus injection is carried out using a 2% solution of the therapeutic agent.

According to another preferred embodiment the continuous intravenous injection is carried out having the therapeutic agent dissolved in a 5% dextrose solution.

According to a further preferred embodiment of the invention 2-amino-2,6-propionoxylidide is administered orally. The above given compounds are represented by the general formula

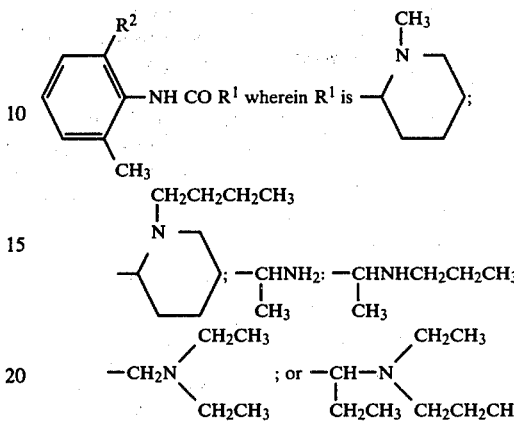

and $R^2$ is hydrogen or methyl whereby $R^2$ is hydrogen when $R^1$ is

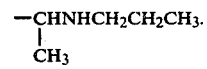

1-methyl-2-(2',6'-xylylcarbomoyl)piperidine is also known under the generic name mepivacaine and is sold under the trade mark Carbocaine ®.

1-butyl-2-(2',6'-xylylcarbamoyl)piperidine is also known under the generic name bupivacaine and is sold under the trade mark Marcaine ®.

2-amino-2',6'-propionoxylidide is also known under the generic name tocainide.

2-propylamino-N-(2'-tolyl)propionamide is also known under the generic name prilocaine and is sold under the trade mark Citanest ®.

Diethylaminoacet-2',6'-xylidide is also known under the generic name lidocaine and is sold under the trade mark Xylocaine ®.

2-ethylpropylamino-2',6'-n-butyroxylidide is also known under the generic name etidocaine and the trade mark Duranest ®.

The expression "therapeutically acceptable salt" is recognised in the art to designate an acid addition salt, which is physiologically innocuous when administered in a dosage and at an interval (e.g. frequency of administration) that is effective for the indicated therapeutic use of the parent compound. Typical therapeutically acceptable acid addition salts of the above given compounds include, but are not limited to the salts of mineral acids such as hydrochloric, phosphoric or sulphuric acid, and of organic acids such as succinic and tartaric acids, and sulphonic acids such as methane sulphonic acid.

In clinical practice the therapeutic agents of the invention will normally be administered orally or by injection in the form of pharmaceutical prepartions comprising the active ingredient in the form of the free base or one of the common therapeutically acceptable salts, e.g., the hydrochloride, in association with a pharmaceutically acceptable carrier which may be a solid, semi-solid or liquid diluent or an ingestible capsule. Usually the active substance will comprise between 0.1% and 10% by weight of the preparation as, for example, in a water solution in the form of its soluble acid salt although when present in the form of solid preparations, i.e., tablets or capsules, the concentration of the compounds of the claimed invention may be present up to 100% by weight of the tablet or capsule.

Pharmaceutical preparations in the form of dosage units of 100 to 250 mg. each for oral application may be formed by mixing either the base or acid salt form with a solid, pulverulent carrier. Examples are lactose, saccharose, sorbitol, mannitol, and starches such as potato starch, corn starch or amylopectin, cellulose derivatives, and gelatin. The carrier may also be lubricants such as magnesium or calcium stearate, a Carbowax or other polyethylene glycol wax compressed to form tablets or cores which can then be coated with either a concentrated sugar solution which may also contain gum arabic, gelatin, talcum and/or titanium dioxide, or which may be coated alternatively with a lacquer dissolved in a readily volatile organic solvent or mixture of organic solvents. Dyestuffs can be added to these coatings. Sustained release tablets are obtained by using several layers of the active drug, separated by slowly dissolving coatings. Another way of preparing sustained release tablets is to divide the dose of the active drug into granules with coatings of different thicknesses and compress the granules into tablets together with the carrier substance. The active substance can also be incorporated in slowly-dissolving tablets made from fat and wax substances, or it may be evenly distributed in a tablet or an insoluble substance such as a physiologically inert plastic substance such as described in Fryklof U.S. Pat. No. 3,317,394.

Soft gelatin capsules (pearl-shaped closed capsules) and other closed capsules consist, for example, of a mixture of gelatin and glycerol, and can contain mixtures of the active substance with a vegetable oil. Hard gelatin capsules contain granulates of the active substance with solid, pulverulent carriers such as lactose, saccharose, sorbitol, mannitol, or starches such as potato starch, corn starch or amylopectin, or cellulose derivatives or gelatin, as well as magnesium stearate or stearic acid. The dosage unit for all these capsules may range between 100 and 250 mg. for either the base or acid addition salt.

For parenteral application by injection the preparations of the invention advantageously comprise an aqueous solution of a water-soluble, pharmaceutically acceptable acid salt of the active substance and optionally also contain a stabilizing agent and/or a buffer substance. The solutions may be made isotonic by the addition of sodium chloride. The preferred dosage unit for these solutions is also 100 to 250 mg. of the therapeutic agent or its therapeutically acceptable salts.

The invention will be described below with reference to Examples and Clinical Trial.

EXAMPLE 1

A syrup containing 2% (weight per volume) of active substance was prepared from the following ingredients:

| | |
|---|---|
| 2-Amino-2',6'-propionoxylidide . HCl | 2.0 g |
| Saccharine | 0.6 g |
| Sugar | 30.0 g |
| Glycerine | 5.0 g |
| Flavouring agent | 0.1 g |
| Ethanol 96% | 10.0 ml |
| Distilled water | ad 100.0 ml |

Sugar, saccharine and the xylidide salt were dissolved in 60 g of warm water. After cooling, glycerine and a solution of flavouring agents dissolved in ethanol were added. To the mixture, water was then added to 100 ml.

The above-given active substance may be replaced with other physiologically acceptable acid addition salts of this or the other therapeutic agents given.

EXAMPLE 2

2-amino-2',6'-propionoxylidide hydrochloride (250 g) was mixed with lactose (175.8 g), potato starch (169.7 g) and colloidal silicic acid (32 g). The mixture was moistened with a 10% solution of gelatine and was granulated through a 12-mesh sieve. After drying, potato starch (160 g), talc (50 g) and magnesium stearate (5 g) were admixed and the mixture thus obtained was pressed into tablets (10,000) which contain 25 mg of substance. The tablets are sold on the market provided with a breaking score to give another dose than 25 mg or to give multiples thereof when broken.

EXAMPLE 3

Granules were prepared from 2-amino-2',6'-propionoxylidide-hydrochloride (250 g), lactose (175.9 g) and an alcoholic solution of polyvinylpyrrolidone (25 g). After the drying step, the granules were mixed with talc (25 g), potato starch (40 g) and magnesium stearate (2.50 g) and was pressed into 10,000 biconvex tablets. These tablets are primarily coated with a 10% alcoholic solution of shellac and thereupon with an aqueous solution containing saccharose (45%), gum arabic (5%), gelatine (4%) and dyestuff (0.2%). Talc and powder sugar were used for powdering after the first five coatings. The coated tablets were then coated with a 66% sugar syrup and polished with a 10% carnauba wax solution in carbon tetrachloride.

EXAMPLE 4

2-Propylamino-N-(2'-tolyl)propionamide-hydrochloride (1 g), sodium chloride (0.8 g) and ascorbic acid (0.1 g) were dissolved in sufficient amount of distilled water to give 100 ml of solution. This solution, which contains 10 mg of active substance in each ml, was used for filling ampoules, which were sterilized by heating at 120° C. for 20 minutes.

Clinical trials

Elective hips surgery is complicated by a high incidence of deep venous thrombosis and the major veins of the thigh are often involved. Thus this operation provides a suitable model to confirm or refute the hypothesis that prevention of white cell adhesion and migration of leucocytes will significantly reduce the incidence of deep venous thrombosis in major veins.

With their full co-operation and consent 34 patients were studied. Control (C) and treatment (L) groups were formed by random selection. The control group consisted of 14 patients and the treatment group consisted of 20 patients. Pre-operative assessment included ECG and erect and supine plain chest X-ray. Patients with previously well-documented thrombo-embolism (1 in the control group, and 3 in the treatment group), prior hip surgery (2 in the control group, and 4 in the treatment group) were not excluded. None had a cardiac dysrhythmia or demonstrable allergy to lidocaine. A routine Charnley total hip arthoplasty was performed by the same surgical team and postoperative care and physiotherapy, including the encouragement and supervision of contraction of the leg muscles was the same in each case.

Prophylaxis: Intravenous infusion of lidocaine in a 5% dextrose solution via a Drum catheter was commenced 2 hrs prior to surgery and continued for six days, the infusion being stopped at the time of the first postoperative phlebograph. An intravenous bolus of 2 percent lidocaine (1 mg/kg body weight) was given prior to the commencement of the continuous infusion, which latter was controlled by means of a drip rate meter (IVAC 503) to maintain rate of delivery of 2 mg of lidocaine per minute. The control group was transfused with a 5% dextrose solution only, for the same period postoperatively.

Diagnosis of deep venous thrombosis: Thermography: Thermographic scanning of the legs was performed preoperatively and postoperatively daily until discharge. Typical appearances in deep venous thrombosis have been previously described and the accuracy of the method is well documented.

Phlebography: Percutanous ascending functional phlebography was performed preoperatively and, on positive thermographic findings, postoperatively, or, if the thermographs remained normal, on the 6th and 14th postoperative days, using the usual criteria for the diagnosis of venous thrombosis. An unbiased opinion was also obtained from an experienced radiologist, who was unaware of the trial.

Blood lidocaine levels: A sample of blood was taken for estimation of blood lidocaine levels immediately after delivery of the bolus injection and at the same time on the 1st, 2nd, and 6th days during the infusion and 24 hrs after the infusion was stopped.

When the trial was planned, because of the fundamental nature of the study and the close supervison given to each patient, it was considered both necessary and ethical to have for comparison two well-matched but randomly allocated groups, one receiving no prophylaxis and the other receiving the trial substance. The original intention was to perform a study with a minimum of 20 cases in each group. However, the high incidence of deep venous thrombosis and pulmonary embolism, documented by perfusion lung scanning after heparin therapy had been started, in the control group, after 14 cases had been studied, indicated that the control group had to be terminated at it was no longer ethical to continue. Thus 14 cases in the control group and 20 cases in the treatment group were available for comparison.

In the treatment group the following results were obtained.

4 patients developed small areas of thrombosis and in only 1 of these it involved veins above the posterior tibial vein as confirmed by venography on the 7th day. Venography of the treatment group on the 14th postoperative day showed thrombosis in the thigh veins in 4 patients and in the lower leg veins in a further 7 patients.

In the control group the following results were obtained:

11 patients suffered from vein thrombosis, 8 of these showing vein thrombosis in the thigh veins and 2 showing pulmonary embolism.

No pulmonary embolism was diagnosed in the treated group.

As evident from above a significant prevention of the generation of deep venous thrombosis is obtained compared with no prophylactic treatment after surgery in the lower parts of the body.

I claim:

1. A method for prophylactic prevention of postoperative deep venous thrombosis in mammals, including man, which are to be subjected to surgical incisions, whereby a therapeutically effective amount of a compound selected from the group consisting of 2-amino-2',6'-propionoxylidide and diethylaminoacet-2',6'-xylidide, or a therapeutically acceptable salt thereof is administered.

2. A method according to claim 1, wherein the therapeutic agent is administered intravenously.

3. A method according to claim 2 wherein the therapeutic agent is administered continuously at a rate of 2 mg/minute from 2 hrs pre surgery and to 144 hrs post surgery.

4. A method according to claim 2 wherein the therapeutic agent is administered as an intravenous bolus administration of 1 mg per kg bodyweight 2 hrs pre surgery, followed by a continuous intravenous administration of 2 mg/minute from 2 hrs pre surgery to 144 hrs post surgery.

5. A method according to claim 4, wherein the bolus administration is carried out using a 2% solution of the therapeutic agent.

6. A method according to claim 2, wherein the continuous intravenous administration is carried out having the therapeutic agent dissolved in a 5% dextrose solution.

7. A method according to claim 1, wherein 2-amino-2',6'-propionoxylidide is administered orally.

* * * * *